(12) United States Patent
Wagner et al.

(10) Patent No.: US 7,110,811 B2
(45) Date of Patent: Sep. 19, 2006

(54) METHOD AND APPARATUS FOR ATRIAL TACHYARRHYTHMIA CARDIOVERSION

(75) Inventors: Darrell O Wagner, Isanti, MN (US); Hugo X. Gonzalez, Woodinville, WA (US); Willis A. Tacker, Jr., Sammamish, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 558 days.

(21) Appl. No.: 10/334,696

(22) Filed: Dec. 30, 2002

(65) Prior Publication Data

US 2004/0127946 A1    Jul. 1, 2004

(51) Int. Cl.
*A61N 1/39* (2006.01)

(52) U.S. Cl. .............................. 607/4; 607/5

(58) Field of Classification Search ............... 607/4–5
See application file for complete search history.

(56) References Cited

U.S. PATENT DOCUMENTS

| | | | |
|---|---|---|---|
| 4,895,151 A | 1/1990 | Grevis et al. | |
| 5,083,562 A | 1/1992 | de Coriolis et al. | |
| 5,405,363 A | 4/1995 | Kroll et al. | |
| 5,620,468 A * | 4/1997 | Mongeon et al. | 607/5 |
| 5,713,924 A * | 2/1998 | Min et al. | 607/4 |
| 5,814,079 A | 9/1998 | Kieval | |
| 5,928,271 A * | 7/1999 | Hess et al. | 607/14 |
| 5,993,443 A | 11/1999 | Murphy-Chutorian et al. | |
| 6,001,091 A | 12/1999 | Murphy-Chutorian et al. | |
| 6,091,991 A | 7/2000 | Warren | |
| 6,128,529 A | 10/2000 | Elser | |
| 6,157,859 A | 12/2000 | Alt | |
| 6,292,696 B1 | 9/2001 | Warren | |
| 6,393,321 B1 | 5/2002 | Warren | |
| 6,430,438 B1 | 8/2002 | Chen et al. | |
| 6,456,871 B1 | 9/2002 | Hsu et al. | |
| 6,512,951 B1 | 1/2003 | Marcovecchio et al. | |
| 6,584,350 B1 | 6/2003 | Kim et al. | |
| 6,687,541 B1 | 2/2004 | Marcovecchio et al. | |
| 6,704,597 B1 | 3/2004 | Ware et al. | |
| 6,721,596 B1 | 4/2004 | Girouard et al. | |
| 6,757,562 B1 | 6/2004 | Baker et al. | |
| 6,847,842 B1 | 1/2005 | Rodenhiser et al. | |
| 6,873,873 B1 | 3/2005 | Hsu et al. | |
| 2002/0147468 A1 | 10/2002 | Kim et al. | |
| 2002/0198461 A1 | 12/2002 | Hsu et al. | |
| 2003/0004551 A1 | 1/2003 | Chen et al. | |
| 2003/0135242 A1 * | 7/2003 | Mongeon et al. | 607/5 |
| 2004/0015192 A1 | 1/2004 | Kim et al. | |
| 2004/0098059 A1 | 5/2004 | Chen et al. | |
| 2004/0127948 A1 | 7/2004 | Stahmann et al. | |
| 2004/0172076 A1 | 9/2004 | Stahmann et al. | |
| 2004/0215245 A1 | 10/2004 | Stahmann et al. | |
| 2004/0243191 A1 | 12/2004 | Baker et al. | |
| 2005/0010257 A1 | 1/2005 | Lincoln et al. | |
| 2005/0027318 A1 | 2/2005 | Ware et al. | |
| 2005/0065563 A1 | 3/2005 | Scheiner | |

(Continued)

*Primary Examiner*—Carl Layno
(74) *Attorney, Agent, or Firm*—Schwegman, Lundberg, Woessner, & Kluth, P.A.

(57) ABSTRACT

An apparatus and method for delivering electrical shock therapy in order to treat atrial tachyarrhythmias such as atrial fibrillation is presented. The ventricular rhythm of certain patients during an episode of atrial fibrillation may be such that shockable R—R intervals are infrequent or do not occur at all. Continuous electrical stimulation of the atria after detection of an atrial tachyarrhythmia may be utilized to modify the ventricular rhythm in such patients to increase the frequency of shockable R—R intervals.

30 Claims, 6 Drawing Sheets

U.S. PATENT DOCUMENTS

2005/0096703 A1   5/2005   Sanders
2006/0025822 A1   2/2006   Zhang

\* cited by examiner

METHOD AND APPARATUS FOR ATRIAL TACHYARRHYTHMIA CARDIOVERSION

FIELD OF THE INVENTION

This disclosure pertains to methods for treating atrial tachyarrhythmias. In particular, the disclosure relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include ventricular tachycardia, ventricular fibrillation, atrial tachycardia, and atrial fibrillation. Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Cardioversion refers to a shock delivered synchronously with a ventricular beat, while defibrillation refers to an asynchronously delivered shock. Implantable cardioverter/defibrillators (ICDs) provide this kind of therapy by delivering a shock pulse to the heart when fibrillation is detected by the device. An ICD is an electronic device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and may also incorporate cardiac pacing functionality.

The most dangerous tachyarrhythmias are ventricular tachycardia and ventricular fibrillation, and ICDs have most commonly been applied in the treatment of those conditions. Ventricular fibrillation is treated by the immediate delivery of a defibrillation shock, while ventricular tachycardia can be treated with either a defibrillation or a cardioversion shock. ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrioventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As aforesaid, an ICD terminates atrial fibrillation by delivering a shock pulse to electrodes disposed in or near the atria. The resulting depolarization also spreads to the ventricles, however, and there is a risk that such an atrial shock pulse can actually induce ventricular fibrillation, a condition much worse than atrial fibrillation. To lessen this risk, the ICD delivers a cardioversion shock synchronously with a sensed ventricular depolarization (i.e., an R wave) and delays delivering the shock until the intrinsic ventricular rhythm is below a specified maximum rate. That is, an R—R interval, which is the time between a presently sensed R wave and the preceding R wave, is measured. If the R—R interval is above a specified minimum value, the interval is considered shockable and the atrial cardioversion shock pulse is delivered.

If the ventricular rhythm does not slow to a safe rate in a short time, however, the delay in delivering atrial cardioversion therapy may be deleterious to the patient. In addition, a particular subset of patients have spontaneous ventricular rhythms during atrial tachyarrhythmias that may remain too rapid to ever safely deliver an atrial cardioversion shock, and these patients may not be suitable candidates for ICD therapy. What is needed in the art is a system which addresses these and other problems.

SUMMARY

The present system provides method and apparatus for stimulating the heart where the ventricular rhythm during an atrial tachyarrhythmia is altered by atrial electrical stimulation which affects the rate at which excitation is conducted from the atria to the ventricles. A device may be configured to initiate such atrial stimulation upon detection of an atrial tachyarrhythmia, where the stimulation is applied continuously during one or more cardiac cycles in the form of a DC voltage or burst pacing at a pre-specified frequency. The atrial stimulation has the effect of increasing the probability that a shockable R—R interval will occur so that an atrial cardioversion pulse may be safely delivered.

This summary is intended not to limit the claimed subject matter, and the scope of the invention is defined by attached claims and their equivalents.

DETAILED DESCRIPTION

The present invention is a method and apparatus for treating atrial tachyarrhythmias such as atrial flutter and atrial fibrillation by altering the ventricular rhythm with atrial stimulation in order to safely deliver an atrial cardioversion shock. The invention may be incorporated into an implantable cardiac rhythm management device as described below.

1. Exemplary Device Description

Figure 1:
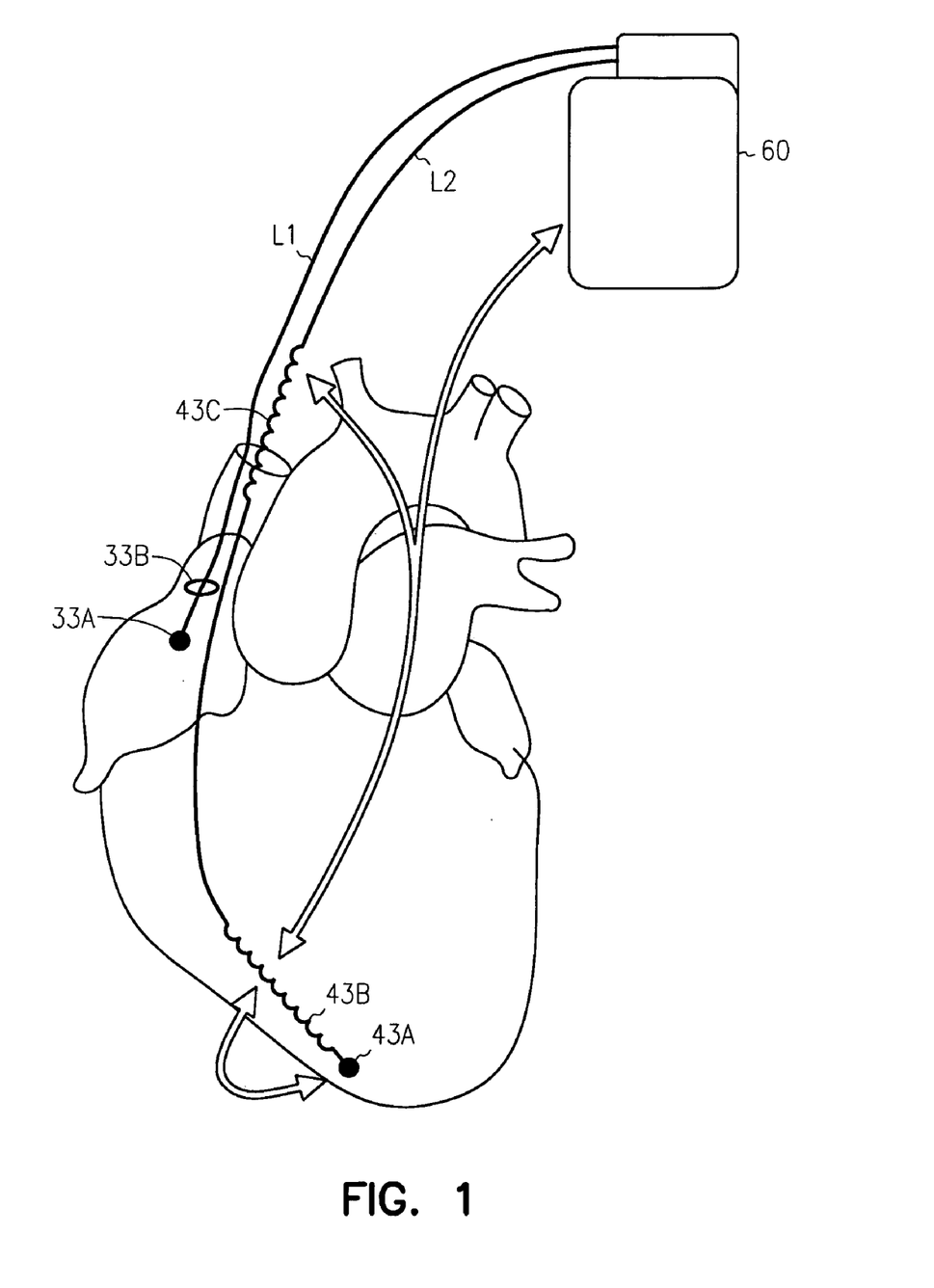
FIG. 1 depicts an exemplary physical configuration of an implanted cardiac rhythm management device.

Cardiac rhythm management devices such as ICDs and pacemakers are typically implanted subcutaneously on a patient's chest and have leads threaded intravenously into the heart to connect the device to electrodes used for sensing cardiac activity, delivering pacing pulses, and/or delivering defibrillation shocks. FIG. 1 depicts an implantable device which includes a subcutaneously implantable housing or can 60 for enclosing the electronic circuitry of the device and a pair of leads L1 and L2 having electrodes incorporated therein. The lead L1 has a tip electrode 33a and ring electrode 33b which are shown in the figure as disposed in the right atrium for pacing and/or sensing of the atria. The lead L2 has a tip electrode 43a, a distal coil electrode 43b, and a proximal coil electrode 43c. Coil electrodes can be used to deliver pacing pulses but are designed especially for delivering cardioversion/defibrillation shocks. In the placement of the lead L2 shown in the figure, tip electrode 43a and distal coil electrode 43b are disposed in the right ventricle (RV), and proximal coil electrode 43c is disposed in the superior vena cava or right atrium. Sensing or pacing of the ventricles may be performed using tip electrode 43a and/or coil electrode 43b. An atrial or ventricular cardioversion/defibrillation shock may be delivered between coil 43b and the can 60, or between coil 43b and the can 60 electrically in common with the coil 43c. Other embodiments may employ an additional coil electrode in the right atrium and/or coronary sinus for delivering an atrial cardioversion shock.

Figure 2:
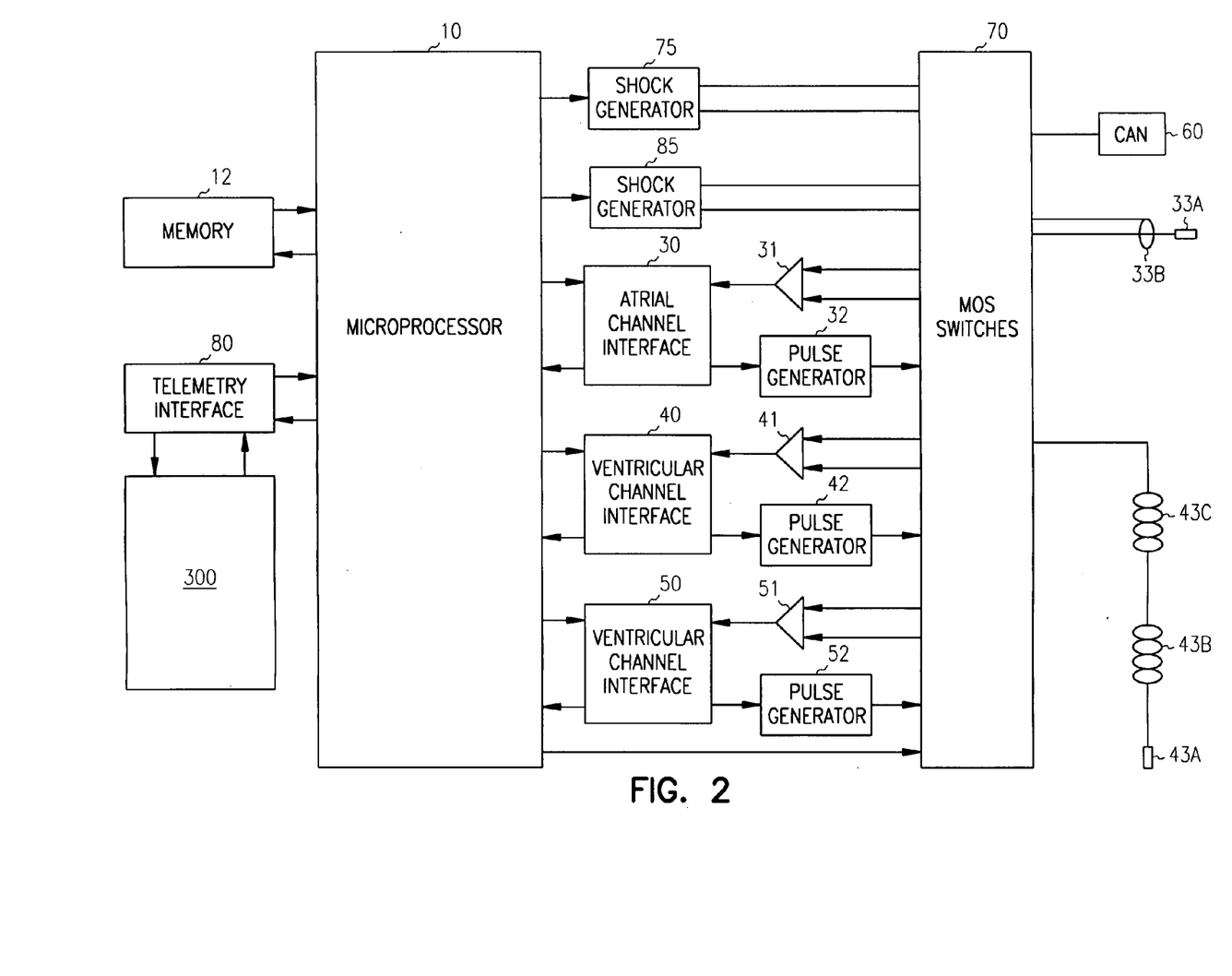
FIG. 2 is a system diagram of an implantable cardiac rhythm management device.

FIG. 2 is a system diagram of a microprocessor-based implantable cardioverter/defibrillator device for treating atrial and ventricular tachyarrhythmias that also incorporates functionality for pacing the atria and/or the ventricles. The controller of the device is made up of a microprocessor 10 communicating with a memory 12, where the memory 12 may comprise a ROM (read-only memory) for program storage and a RAM (random-access memory) for data storage. A microprocessor-type controller 10 controls the overall operation of the device in accordance with programmed instructions stored in memory. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. A telemetry interface 80 is provided for communicating with an external programmer 300. The external programmer is a computerized device with a controller that can interrogate the device and receive stored data as well as adjust the device's operating parameters.

The device is equipped with multiple sensing amplifiers and pulse generators which can be configured as channels for pacing and/or sensing selected heart chambers. A MOS switch matrix 70 controlled by the microprocessor is used to configure a sensing or pacing channel by switching selected electrodes to the input of a sense amplifier or to the output of a pulse generator. The switch matrix 70 also allows the device to employ either bipolar sensing/pacing using two closely spaced electrodes of a lead or unipolar sensing/pacing using one of the electrodes of a lead and the can 60 as a reference electrode. In the device shown in FIG. 2, an atrial channel for sensing or pacing an atrial site is configured with tip electrode 33a, ring electrode 33b, sense amplifier 31, pulse generator 32, and an atrial channel interface 30 which communicates bidirectionally with a port of microprocessor 10. A first ventricular channel for sensing or pacing a ventricular site is configured with tip electrode 43a, coil electrode 43b, sense amplifier 41, pulse generator 42, and ventricular channel interface 40. A second ventricular sensing channel using ventricular channel interface 50 may be configured by connecting one of the differential inputs of sense amplifier 51 to the coil electrode 43b and connecting the other input to the can 60 and coil electrode 43c. The switch matrix 70 can also connect atrial shock generator 75 or ventricular shock generator 85 to deliver an atrial or ventricular cardioversion/defibrillation shock between coil electrode 43b and the can 60 (or the can 60 connected in common with the coil electrode 43c).

The channel interfaces may include comparators for comparing received electrogram signals to reference values, analog-to-digital converters for digitizing sensing signal inputs from the sensing amplifiers, registers that can be written to for adjusting the gain and threshold values of the sensing amplifiers, and registers for controlling the output of pacing pulses and/or adjusting the pacing pulse energy by changing the pulse amplitude or pulse width. The controller uses the sensing channels in order to detect intrinsic cardiac activity in a heart chamber, referred to as a chamber sense (e.g., an atrial sense or a ventricular sense). In order to detect intrinsic cardiac activity, the signals emanating from the sense amplifier are compared with a reference potential. As described above, a sensing channel includes sense amplifier circuits for amplifying and filtering the electrogram signals picked up by an electrode disposed at a cardiac site. Only when an electrogram signal from the sense amplifier exceeds a reference potential threshold will it be treated as a chamber sense. The reference potential may thus be referred to as a sensing threshold. The sensing threshold may be implemented with analog circuitry, where the sense amplifier output is applied to one input of a comparator circuit whose other input is connected to a reference potential, or with digital circuitry operating on digitized samples of the sense amplifier output which are compared with a digitized reference value. In either case, the sensing threshold for each channel is adjustable by the controller.

Detected chamber senses may be used for controlling the delivery of paces in accordance with a programmed pacing mode and/or for diagnostic purposes. In an inhibited demand pacing mode, for example, chamber senses are used to inhibit pacing, while in a triggered pacing mode chamber senses are used to trigger pacing pulses. By counting the number of chamber senses over a defined time period, the controller is also able to measure heart rate and detect arrhythmias using a rate-based criterion. The device detects an atrial tachyarrhythmia, for example, by measuring the atrial rate as well as possibly performing other processing on data received from the atrial sensing channel. Ventricular tachyarrhythmias may be similarly detected using a ventricular sensing channel.

2. Atrial Cardioversion Shock Therapy

In order to avoid the possible induction of ventricular fibrillation, atrial shocks should be delivered synchronously with a sensed R wave and after a minimum (and possibly maximum) pre-shock R—R interval. The R—R interval is the time between the immediately preceding R wave and the presently sensed R wave, and an R wave may be regarded as either a spontaneously occurring depolarization or a ventricular pace. Shocking synchronously with an R wave is done because the ventricle is especially vulnerable to induction of fibrillation by a depolarizing shock delivered at a time too near the end of the preceding ventricular contraction (i.e., close to the T wave on an EKG). Delivering the shock synchronously with a sensed R wave thus moves the shock away from the vulnerable period, but at a very rapid ventricular rhythm, the ventricular beats may be so close together that even synchronously delivered shocks may induce ventricular fibrillation. Shocking should therefore be delayed until the ventricular rhythm is slow enough to safely deliver the cardioversion pulse as determined by measuring the R—R interval.

The device depicted in FIG. 2 can be configured to deliver atrial cardioversion therapy by appropriate programming of the microprocessor. Thus, once an atrial tachyarrhythmia is detected with the atrial sensing channel, the device prepares to deliver an atrial cardioversion shock. The ventricular rhythm is monitored by measuring the R—R interval associated with each sensed R wave. If a sensed R wave occurs at an R—R interval longer than a specified minimum limit value (e.g., 500 ms), the interval is considered shockable so that the sensed R wave is safe to shock on. An atrial cardioversion shock is then delivered immediately so as to be practically synchronous with the sensed R wave. The process may be repeated until the atrial tachyarrhythmia is terminated.

3. Ventricular Rate-Altering Atrial Stimulation

The intrinsic ventricular rhythm that occurs during an atrial tachyarrhythmia is a result of the chaotically occurring depolarizations occurring in the atria being passed through the AV node to the ventricles. The intrinsic ventricular rate is thus governed by the cycle length of the atrial tachyarrhythmia and the refractory period of the AV node, and the intrinsic ventricular rhythm during atrial fibrillation tends to be both rapid and irregular. Due to irregularity of the rhythm, a shockable R—R interval can occasionally occur even though the average ventricular rate is higher. In atrial flutter and some types of atrial fibrillation, however, the ventricular rhythm is rapid but not irregular. In those instances, shockable R—R intervals may rarely or never spontaneously occur.

In order to deal with this situation, an implantable device such as illustrated in FIGS. 1 and 2 may be programmed to deliver continuous atrial stimulation during an atrial tachyarrhythmia in order to alter the ventricular rate while continuing to monitor for a shockable R—R interval. Such ventricular rate-altering atrial stimulation may be applied to the right atrium through the atrial pacing channel in the form of either burst pacing or a DC voltage of a specified amplitude (e.g., a pulse amplitude or DC voltage between 0.5 and 9 volts), where the stimulation is delivered continuously throughout one or more cardiac cycles. The stimulation alters the ventricular rate by affecting the rate at which atrial depolarizations are conducted across the atrio-ventricular node and tends to make the ventricular rhythm more irregular, thus increasing the probability of a shockable R—R interval. Ventricular rate-altering atrial stimulation may thus either shorten the time after detection of an atrial tachyarrhythmia until a shock pulse can be delivered or, in some cases, may make safe delivery of an atrial cardioversion shock pulse possible where it would not be otherwise.

Figure 3:
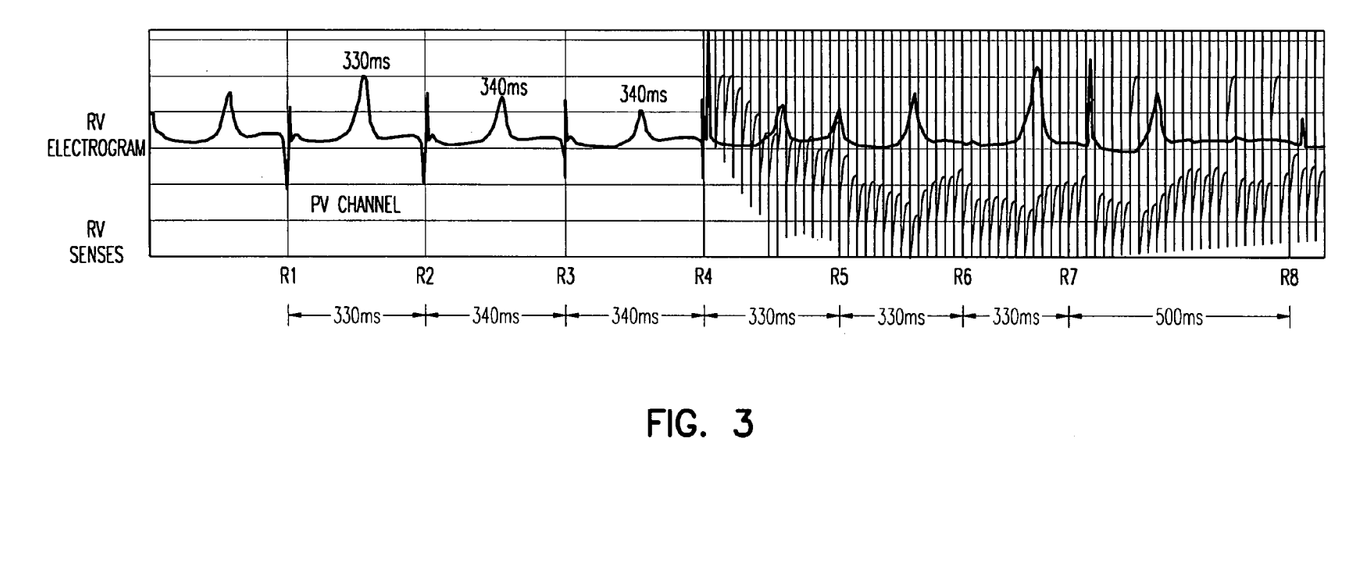
FIG. 3 illustrates an example of ventricular rate-altering atrial stimulation.
Figure 6:
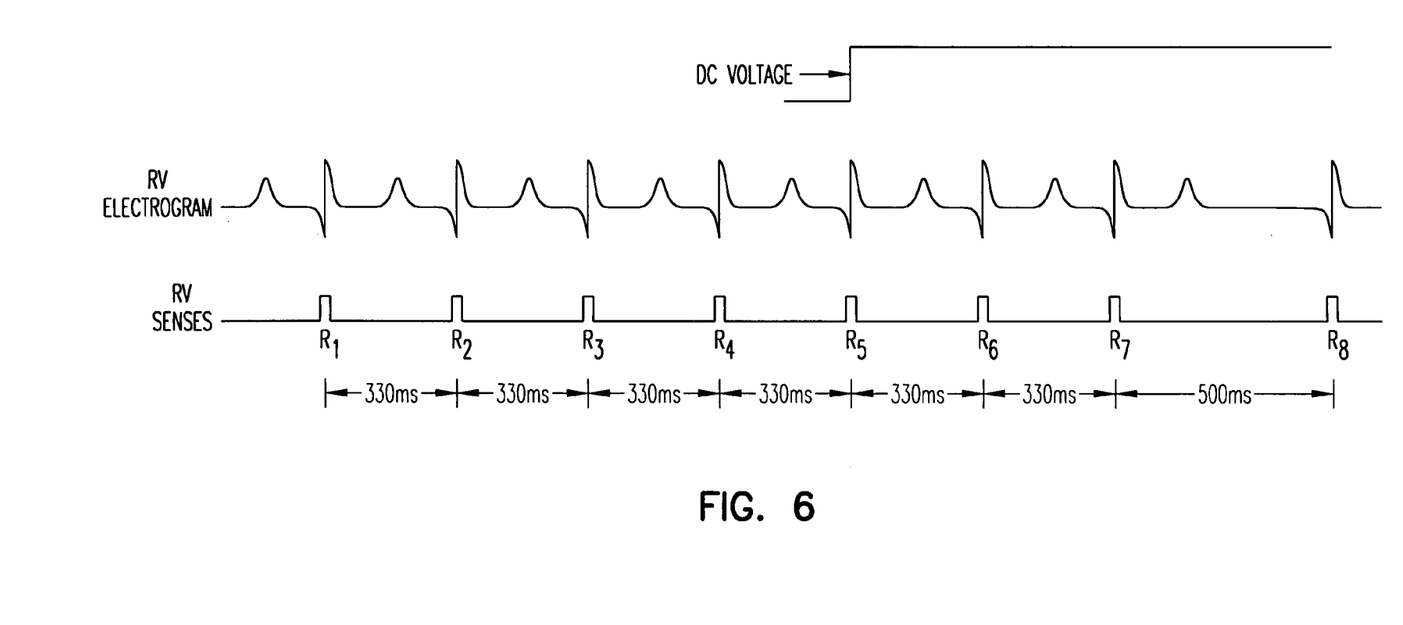
FIG. 6 illustrates an example of ventricular rate-altering stimulation using DC stimulation.

FIG. 3 illustrates the application of ventricular rate-altering therapy where the atrial stimulation is delivered in the form of burst pacing at approximately 50 Hz. Shown in the figure are an RV (right ventricular) electrogram and resulting RV senses (i.e., R waves) designated as $R_1$ through $R_8$ during an atrial tachyarrhythmia. In this example, the minimum shockable R—R interval is assumed to be 500 ms. The R—R intervals from $R_1$ to $R_4$ are between 330 and 340 ms so that it is not possible to safely deliver an atrial cardioversion shock. Atrial stimulation is then initiated coincident with $R_4$ which, after a few cycles, results in a shockable R—R interval of 500 ms associated with $R_8$ so that a cardioversion shock may be delivered in synchrony with that R wave. FIG. 6 illustrates a similar example using DC stimulation.

Figure 4:
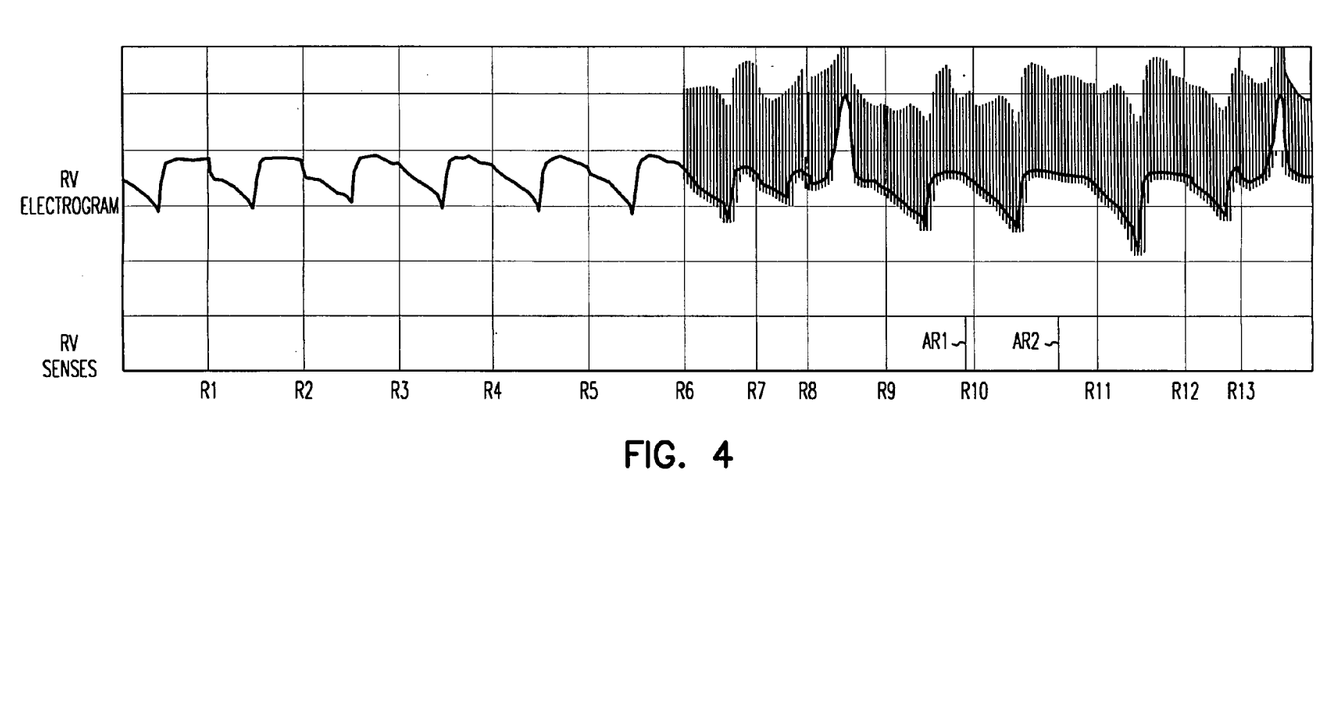
FIG. 4 illustrates false sensing of R—R waves during atrial stimulation.

As mentioned above, ventricular rate-altering atrial stimulation may be delivered in the form of burst pacing or a DC voltage. Application of atrial stimulation as either a pulse train of sufficiently high frequency (e.g., greater than 1 kHz) or a DC voltage would not ordinarily interfere with the simultaneous sensing of R waves since the atrial stimulation would be above or below, respectively, the sense amplifier bandwidth. Application of atrial stimulation as a medium frequency, low-duty cycle pulse train (e.g., pacing pulses at 50 Hz), however, can lead to unreliable R wave sensing as some atrial stimulation pulses may be interpreted as R waves. FIG. 4 illustrates an example of such R wave false sensing during continuous atrial stimulation with a 50 Hz pulse train. Shown in the figure are an RV electrogram and resulting true RV senses designated as $R_1$ through $R_{13}$ during an atrial tachyarrhythmia. Atrial stimulation is initiated coincident with $R_6$ which causes the ventricular sensing channel to also detect artifacts $AR_1$ and $AR_2$ as R waves. False sensing of R waves may thus result in a shockable R—R interval being missed. Also, if an actual R wave is undersensed, false sensing of an atrial stimulation artifact as an R wave may cause the device to deliver a cardioversion shock at a non-shockable R—R interval.

Figure 5:
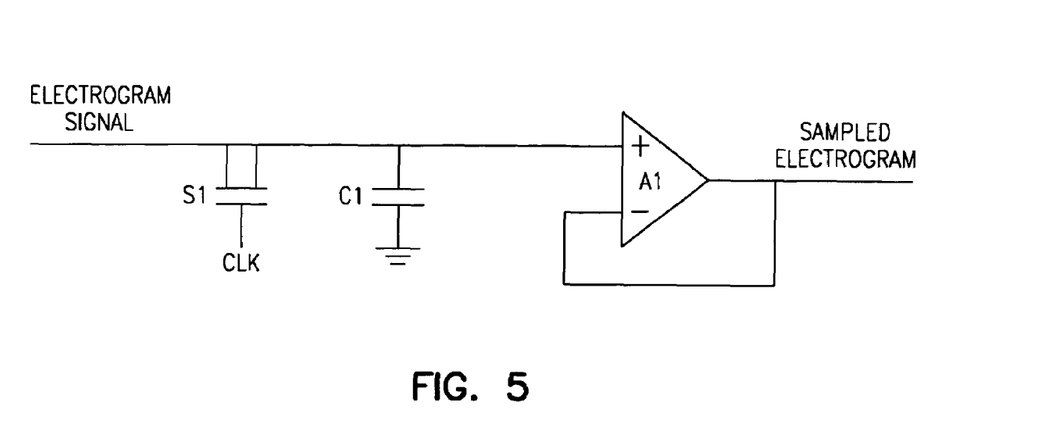
FIG. 5 is an example of a sample-and-hold circuit.

Depending upon how the sensing circuitry of particular device is implemented, several different techniques may be employed to reduce the effects of pulsatile atrial stimulation on R wave sensing. If the frequency of the atrial stimulation pulses is high enough, low-pass filtering of the ventricular electrogram signal to remove the atrial stimulation artifact may be possible while still allowing adequate bandwidth for R wave detection. Another technique is to sample the ventricular electrogram signal prior to R wave detection at sampling instants which occur between pulses of the atrial stimulation pulse train in order to remove the artifact. FIG. 5 shows a simple example of a sample-and-hold circuit made up of a solid-state switch S1, a capacitor C1, and an amplifier A1. The switch S1 is closed for a specified sampling period only when no atrial stimulation pulse is being output, for example, by operating the switch S1 with a clock signal CLK derived from the clock signal used to drive the atrial stimulation pulse generator. Whatever level of the electrogram signal that was present when the switch S1 was closed is held on the capacitor C1 when the switch S1 is opened. If the switch S1 is opened during each atrial stimulation pulse, the artifact is thus removed from the electrogram signal. The resulting sampled electrogram signal may then be further processed before comparing with the sensing threshold. The same principle may be applied in more complicated switched-capacitor circuits which filter the electrogram signal prior to R wave detection. In another embodiment, the sensing amplifier of the ventricular sensing channel is blanked (e.g., by disabling the amplifier or shorting its input to ground) in synchrony with the output of atrial stimulation pulses. If the sensing channel is implemented such that a sampled electrogram signal is digitized prior to R wave detection, digital filtering techniques may be employed as either a primary or secondary means of removing the atrial stimulation artifact.

Another consideration is the timing of the initiation and cessation of atrial stimulation. The sudden application or withdrawal of atrial stimulation during the ventricular vulnerable period may present a risk of inducing a ventricular arrhythmia. It may therefore be desirable to initiate and/or cease atrial stimulation synchronously with an R wave.

Initiation of atrial stimulation may be further constrained by requiring a minimum startable R—R interval before the atrial stimulation can be started. A minimum stoppable R—R interval may similarly be specified which constrains the stopping of atrial stimulation until an R wave is detected which meets that minimum R—R interval criterion. The startable and stoppable R—R intervals would be less than the specified shockable R—R interval but still long enough to provide a margin of safety. For example, the shockable R—R interval may be specified as 500 ms, and the startable and stoppable R—R intervals may be specified as 350 ms. The atrial stimulation may also be stopped synchronously with the delivery of an atrial cardioversion shock upon detection of a shockable R—R interval.

A device such as illustrated in FIGS. 1 and 2 may be programmed to monitor atrial activity through its atrial sensing channel in order to detect atrial tachyarrhythmias and to deliver ventricular rate-altering atrial stimulation using any of the techniques discussed above. When such an atrial tachyarrhythmia is detected, the device may be programmed to immediately initiate atrial stimulation through the atrial channel and wait for a shockable R—R interval to deliver an atrial cardioversion shock. Alternatively, the device may initially attempt to terminate the arrhythmia by delivering atrial anti-tachycardia pacing for a specified time period before starting the atrial stimulation. The device may also be programmed to initially try to deliver an atrial cardioversion shock and initiate atrial stimulation only if a pre-specified number of R waves are detected without the occurrence of a shockable R—R interval or only after some pre-specified time period has elapsed without the occurrence of a shockable R—R interval.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac rhythm management device, comprising:
   detecting an atrial tachyarrhythmia from sensed atrial electrical activity;
   sensing ventricular electrical activity to generate a ventricular electrogram signal and detecting a ventricular sense (R wave) when the ventricular electrogram exceeds a pre-specified threshold;
   delivering continuous atrial stimulation as a pulse train at a frequency greater than approximately 1 kHz while monitoring for R waves;
   measuring an R—R interval for each detected R wave as the time elapsed since an immediately preceding R wave; and,
   delivering an atrial cardioversion shock pulse synchronously with a detected R wave if a shockable R—R interval is measured for that R wave, where a shockable R—R interval is defined as an interval longer than a pre-specified minimum limit value.

2. The method of claim 1 wherein the continuous atrial electrical stimulation is a pulse train at a pre-specified frequency and further comprising low-pass filtering the ventricular electrogram signal prior to R wave detection in order to remove artifact produced by the atrial stimulation.

3. The method of claim 1 wherein the continuous atrial electrical stimulation is a pulse train at a pre-specified frequency and further comprising sampling the ventricular electrogram signal prior to R wave detection at sampling instants which occur between pulses of the atrial stimulation pulse train in order to remove artifact produced by the atrial stimulation pulses.

4. The method of claim 3 further comprising blanking a sense amplifier of a ventricular sensing channel at sampling instants in synchrony with pulses of the atrial stimulation pulse train.

5. The method of claim 3 further comprising digitizing the ventricular electrogram signal prior to R wave detection.

6. The method of claim 5 further comprising filtering the digitized ventricular electrogram signal in order to remove atrial stimulation artifact prior to R wave detection.

7. The method of claim 3 further comprising sampling the ventricular electrogram signal prior to R wave detection using a sample-and-hold technique.

8. The method of claim 1 further comprising initiating the continuous atrial stimulation synchronously with a detected R wave.

9. The method of claim 8 further comprising initiating the continuous atrial stimulation synchronously with a detected R wave only if the R—R interval for that R wave is greater than a pre-specified startable R—R interval.

10. The method of claim 1 further comprising stopping the continuous atrial stimulation synchronously with a detected R wave.

11. The method of claim 10 further comprising stopping the continuous atrial stimulation synchronously with a detected R wave only if the R—R interval for that R wave is greater than a pre-specified stoppable R—R interval.

12. The method of claim 1 further comprising stopping the continuous atrial stimulation synchronously with a delivered atrial cardioversion shock.

13. The method of claim 1 further comprising detecting a pre-specified number of R waves without occurrence of a shockable R—R interval before initiating delivery of the continuous atrial stimulation.

14. The method of claim 1 further comprising initiating atrial stimulation only after a specified time period has elapsed without occurrence of a shockable R—R interval.

15. An apparatus for delivering atrial defibrillation therapy, comprising:
   an atrial sensing channel for sensing atrial electrical activity and generating an atrial electrogram signal;
   a ventricular sensing channel for sensing ventricular electrical activity and generating a ventricular electrogram signal;
   an atrial stimulation channel;
   a shock pulse generator for generating an atrial cardioversion shock pulse; and,
   a controller interfaced to the shock pulse generator, atrial stimulation channel, and the atrial and ventricular sensing channels for controlling the operation of the device, wherein the controller implements circuitry for detecting an atrial tachyarrhythmia from the atrial electrogram and, upon detection of an atrial tachyarrhythmia, performing operations which include:
   detecting a ventricular sense (R wave) when the ventricular electrogram exceeds a pre-specified threshold;
   delivering continuous atrial stimulation as a pulse train at a frequency greater than approximately 1 Khz while monitoring for R waves;
   measuring an R—R interval for each detected R wave as the time elapsed since an immediately preceding R wave; and,
   delivering the atrial cardioversion shock pulse synchronously with a detected R wave if a shockable R—R interval is measured for that R wave, where a shockable R—R interval is defined as an interval longer than a pre-specified minimum limit value.

16. The apparatus of claim 15 wherein the controller implements circuitry for starting delivery of continuous atrial stimulation after detection of an atrial tachyarrhythmia only after a pre-specified number of R waves have been detected without a shockable R—R interval.

17. The apparatus of claim 15 wherein the atrial stimulation channel delivers continuous atrial stimulation as a pulse train at a pre-specified frequency and further comprising circuitry for sampling the ventricular electrogram signal prior to R wave detection at sampling instants which occur between pulses of the atrial stimulation pulse train in order to remove artifact produced by the atrial stimulation pulses.

18. The apparatus of claim 17 wherein the ventricular sensing channel includes a sense amplifier and further comprising circuitry for blanking the ventricular channel sense amplifier at sampling instants in synchrony with pulses of the atrial stimulation pulse train.

19. The apparatus of claim 17 further comprising means for digitizing the ventricular electrogram signal prior to R wave detection.

20. The apparatus of claim 19 further comprising circuitry for filtering the digitized ventricular electrogram signal in order to remove atrial stimulation artifact prior to R wave detection.

21. The apparatus of claim 17 further comprising sample-and-hold circuitry for sampling the ventricular electrogram signal prior to R wave detection.

22. The apparatus of claim 15 further comprising circuitry for initiating the continuous atrial stimulation synchronously with a detected R wave.

23. The apparatus of claim 15 further comprising circuitry for initiating the continuous atrial stimulation synchronously with a detected R wave if the R—R interval for that R wave is greater than a pre-specified startable R—R interval.

24. The apparatus of claim 15 further comprising circuitry for stopping the continuous atrial stimulation synchronously with a detected R wave.

25. The apparatus of claim 15 further comprising circuitry for stopping the continuous atrial stimulation synchronously with a detected R wave if the R—R interval for that R wave is greater than a pre-specified stoppable R—R interval.

26. The apparatus of claim 15 further comprising circuitry for stopping the continuous atrial stimulation synchronously with a delivered atrial cardioversion shock.

27. The apparatus of claim 15 wherein the controller is programmed to detect a pre-specified number of R waves without occurrence a shockable R—R interval before initiating delivery of the continuous atrial stimulation.

28. The apparatus of claim 15 wherein the controller is programmed to initiate atrial stimulation only after a specified time period has elapsed without occurrence of a shockable R—R interval.

29. A method for operating a cardiac rhythm management device, comprising:

detecting an atrial tachyarrhythmia from sensed atrial electrical activity;

sensing ventricular electrical activity to generate a ventricular electrogram signal and detecting a ventricular sense (R wave) when the ventricular electrogram exceeds a pre-specified threshold;

delivering continuous atrial stimulation as a DC voltage while monitoring for R waves;

measuring an R—R interval for each detected R wave as the time elapsed since an immediately preceding R wave; and, delivering an atrial cardioversion shock pulse synchronously with a detected R wave if a shockable R—R interval is measured for that R wave, where a shockable R—R interval is defined as an interval longer than a pre-specified minimum limit value.

30. An apparatus for delivering atrial defibrillation therapy, comprising:

an atrial sensing channel for sensing atrial electrical activity and generating an atrial electrogram signal;

a ventricular sensing channel for sensing ventricular electrical activity and generating a ventricular electrogram signal;

an atrial stimulation channel;

a shock pulse generator for generating an atrial cardioversion shock pulse; and, a controller interfaced to the shock pulse generator, atrial stimulation channel, and the atrial and ventricular sensing channels for controlling the operation of the device, wherein the controller implements circuitry for detecting an atrial tachyarrhythmia from the atrial electrogram and, upon detection of an atrial tachyarrhythmia, performing operations which include:

detecting a ventricular sense (R wave) when the ventricular electrogram exceeds a pre-specified threshold;

delivering continuous atrial stimulation as a DC voltage while monitoring for R waves;

measuring an R—R interval for each detected R wave as the time elapsed since an immediately preceding R wave; and, delivering the atrial cardioversion shock pulse synchronously with a detected R wave if a shockable R—R interval is measured for that R wave, where a shockable R—R interval is defined as an interval longer than a pre-specified minimum limit value.

* * * * *